United States Patent
Everett et al.

(10) Patent No.: US 8,073,202 B2
(45) Date of Patent: *Dec. 6, 2011

(54) METHOD OF BIOIMAGE DATA PROCESSING FOR REVEALING MORE MEANINGFUL ANATOMIC FEATURES OF DISEASED TISSUES

(75) Inventors: Matthew J. Everett, Livermore, CA (US); Scott A. Meyer, Livermore, CA (US); Paul F. Stetson, Piedmont, CA (US); Yan Zhou, Pleasanton, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/709,234

(22) Filed: Feb. 19, 2010

(65) Prior Publication Data

US 2010/0226542 A1 Sep. 9, 2010

Related U.S. Application Data

(63) Continuation of application No. 11/223,549, filed on Sep. 9, 2005, now Pat. No. 7,668,342.

(51) Int. Cl.
*G06K 9/00* (2006.01)
*G11B 9/02* (2006.01)
(52) U.S. Cl. .................... 382/106; 356/482
(58) Field of Classification Search ............ 382/128, 382/129, 130, 131, 132, 133, 134, 106; 600/101, 600/102, 103, 104, 105, 118, 442, 445, 459, 600/356, 383, 400, 401, 402, 587, 592, 595; 128/920, 922; 351/204, 205; 356/482
See application file for complete search history.

(56) References Cited

U.S. PATENT DOCUMENTS

| 4,838,679 | A | | 6/1989 | Bille | |
|---|---|---|---|---|---|
| 5,293,871 | A | * | 3/1994 | Reinstein et al. | 600/442 |
| 5,562,095 | A | * | 10/1996 | Downey et al. | 600/445 |
| 5,861,955 | A | * | 1/1999 | Gordon | 356/511 |

(Continued)

FOREIGN PATENT DOCUMENTS

EP    0 415 683 A2    8/1990

OTHER PUBLICATIONS

M. Adaikkappan et al., "Evaluation of Carotid Atherosclerosis by B'Mode Ultrasonographic Study in Hypertensive Patients Compared with Normotensive Patients," *Ind. J. Radiol. Imag.*, vol. 12 (2002), No. 3, pp. 365-368.

(Continued)

*Primary Examiner* — Abolfazl Tabatabai
(74) *Attorney, Agent, or Firm* — Morrison & Foerster LLP

(57) ABSTRACT

The present invention discloses a method for generating elevation maps or images of a tissue layer/boundary with respect to a fitted reference surface, comprising the steps of finding and segmenting a desired tissue layer/boundary; fitting a smooth reference surface to the segmented tissue layer/boundary; calculating elevations of the same or other tissue layer/boundary relative to the fitted reference surface; and generating maps of elevation relative to the fitted surface. The elevation can be displayed in various ways including three-dimensional surface renderings, topographical contour maps, contour maps, en-face color maps, and en-face grayscale maps. The elevation can also be combined and simultaneously displayed with another tissue layer/boundary dependent set of image data to provide additional information for diagnostics.

34 Claims, 11 Drawing Sheets

U.S. PATENT DOCUMENTS

| | | | | |
|---|---|---|---|---|
| 6,165,142 | A * | 12/2000 | Bar | 600/595 |
| 6,609,793 | B2 * | 8/2003 | Norrby et al. | 351/212 |
| 7,194,117 | B2 * | 3/2007 | Kaufman et al. | 382/128 |
| 7,301,644 | B2 * | 11/2007 | Knighton et al. | 356/479 |
| 7,364,296 | B2 | 4/2008 | Miller et al. | |
| 2005/0096515 | A1 | 5/2005 | Geng | |

OTHER PUBLICATIONS

D-U. Bartsch et al., "Optical Coherence Tomography: Interpretation Artifacts and New Algorithm," *Proc. SPIE Medical Imaging 2004: Image Processing*, vol. 5370 (2004), pp. 2140-2151.

M.A. Choma et al., "Sensitivity advantage of swept source and Fourier domain optical coherence tomographny," *Optics Express*, vol. 11, No. 18, Sep. 8, 2003, pp. 2183-2189.

A. Guirao et al., "Corneal wave aberration from videokeratography: accuracy and limitations of the procedure," *J. Opt. Soc. Am. A*, vol. 17, No. 6, Jun. 2000, pp. 955-965.

H. Ishikawa et al., "Macular Segmentation with Optical Coherence Tomography," *Investigative Ophthalmology & Visual Science*, vol. 46 (2005), No. 6, pp. 2012-2017.

R.H. Webb, "Confocal optical microscopy," *Rep. Prog. Phys.*, vol. 59 (1996), pp. 427-471.

Q. Zhou et al., "Mapping retinal thickness and macular edema by high-speed three-dimensional optical coherence tomography," *Ophthalmic Technologies XIV, Proceedings of SPIE* (Bellingham, Washington), vol. 5314 (2004), pp. 119-125.

* cited by examiner

METHOD OF BIOIMAGE DATA PROCESSING FOR REVEALING MORE MEANINGFUL ANATOMIC FEATURES OF DISEASED TISSUES

PRIORITY

This application is a continuation of U.S. patent application Ser. No. 11/223,549, filed Sep. 9, 2005, which is incorporated herein by reference.

TECHNICAL FIELD OF THE INVENTION

One or more embodiments of the present invention relate generally to methods for optical imaging of biological samples and for processing such images. In particular, the invention is a method for processing a three-dimensional image data set to generate elevation maps of tissue layers relative to a fitted smooth surface, which can provide more diagnostic information than a pure tissue layer thickness map. Maps of elevation may be embodied as three-dimensional surface renderings of elevation, topographical maps, or as color or grayscale maps.

BACKGROUND OF THE INVENTION

Measurement of biological tissue surface contour or layer thickness can provide useful diagnostic information in various applications. For example, arterial plaque thickness is related to the progress of atherosclerosis, carotid vessel wall thickness is also an indicator of cardiovascular disease risk; epidermal layer thickness is an indicator of burn severity.

In ophthalmology, retinal thickness may be abnormally large in cases of retinal edema or traction by membranes in the vitreous humor. On the other hand, the retina may appear thin in cases of atrophic degeneration, chorioretinitis, or trauma to the retina. Meanwhile, changes in retinal thickness may be localized or extend over large areas. In certain cases, the overall contour of the retina may become abnormal. For example, pronounced myopia, particularly due to posterior staphylomas, may create a highly concave retina. Detachment of the retinal pigment epithelium (RPE), subretinal cysts, or subretinal tumors may produce a relative convexity of the retina. Therefore, mapping the retina contour or retinal thickness makes it possible to determine the extent and severity of such conditions and to monitor progress of treatment.

In the past, there are a number of well-established biomedical imaging techniques that have been used for three-dimensional anatomical mapping of the eye, especially the retina, including optical coherence tomography (Zhou, Q. et al. (2004). "Mapping retinal thickness and macular edema by high-speed three-dimensional optical coherence tomography". Ophthalmic Technologies XIV, SPIE, 5314: 119-125), ultrasound (see for example, U.S. Pat. No. 5,293,871, U.S. Pat. No. 5,562,095), and confocal microscopy (see for example, U.S. Pat. No. 4,838,679; R. H. Webb (1996) "Confocal optical microscopy" *Rep. Prog. Phys.* 59 427-471). The three-dimensional data set has also been analyzed to identify layered structures in the tissue using a variety of approaches to image segmentation. (see for example, D. G. Bartsch, et al., (2004) "Optical coherence tomography: interpretation artifacts and new algorithm", *Proc. SPIE Medical Imaging* 2004: *Image Processing*, 5370: 2140-2151; H. Ishikawa, et al., (2005) "Macular Segmentation with Optical Coherence Tomography". *Invest Ophthalmol Vis Sci.;* 46: 2012-201).

These prior art methods measured and/or generated a map of a tissue layer thickness by searching for the borders of the tissue layer structures, figuring out the inner and outer boundaries and then finding the distance between the inner and outer boundaries. However, a major issue associated with a tissue layer thickness map is that it sometimes cannot reveal the diagnostically more meaningful features of a diseased part of the tissue. For example, retina thickness is defined as the vertical distance between the RPE (retinal pigment epithelium) 102 and the ILM (inner limiting membrane) 104 as shown in FIG. 1. A sharp bump 106 of the retina will often be associated with a rise in the RPE 102 as well as the formation of a lesion 108 below the RPE 102, such that the RPE also has a broad rise. As a result, a retina thickness map such as the color coded one shown in FIG. 2, which corresponds to FIG. 1, cannot reveal the substantially raised bump. In fact, the color coded thickness map shows that the thickness will only slightly increase near the bump but then return to normal over it. On the other hand, although a topographic map or contour of the RPE or ILM may reveal the sharp bump better for this illustrated case than the retina thickness map, it would include both the sharp bump and the broader warping of the RPE boundary, making it difficult to separate the effect of the disease from the overall shape of the RPE boundary.

In light of the above, there is a need in the art for a method for generating elevation maps with respect to a reference fitted surface and for using the reference surface as a means of locating three-dimensionally a tissue or a layer or boundary of a tissue such as the retina, in order to provide diagnostically more meaningful information about potential diseased tissue.

The present invention is a novel and non-obvious method wherein a fitted reference surface is used to create an elevation map or image of a tissue layer/boundary with respect to the fitted reference surface. Use of such a fitted surface can minimize the perturbations of the surface associated with disease so as to approximate the tissue surface that would exist if the tissue were normal. By using such a fitted surface, either of the tissue boundary being measured, or a different boundary, the effect of disease or injury is isolated from the overall shape of the tissue of interest, providing improved diagnostic information. In addition to various ways to display the elevation data relative to the fitted reference surface, the invention also combines the elevation data with other maps or images in order to provide more meaningful information for diagnostics.

SUMMARY OF THE INVENTION

One or more embodiments of the present invention satisfy one or more of the above-identified needs in the art. In particular, one embodiment of the present invention is a method for generating elevation maps or images of a tissue layer/boundary with respect to the location of a fitted reference surface, comprising the steps of finding and segmenting a desired tissue layer/boundary; fitting a smooth reference surface to the segmented tissue layer/boundary; calculating elevations of the same or other tissue layer/boundary relative to the fitted reference surface; and generating maps of elevation relative to the fitted surface.

One aspect of the present invention is to display the elevation in various ways including three-dimensional surface renderings, topographical contour maps, contour maps, en-face color maps, and en-face grayscale maps.

Another aspect of the present invention is to combine and hence simultaneously display on the same map and/or image two sets of data with one set from the elevation relative to a fitted reference surface and the other set from a tissue layer/boundary dependent information, including, for example, actual thickness of a tissue layer, and image signal strength such as reflectance from an OCT system, birefringence from a polarization sensitive OCT system or a scanning laser polarimetry system, and intensity from a confocal imaging system.

Another aspect of the present invention is to perform the fitting to obtain the reference surface in a number of ways, including using a second-order polynomial fit, or using Zernike or Chebyshev or other polynomials, or Bessel functions, or a portion of a sphere or spheroid. Additionally, the fitting can also be performed by excluding certain portions of the tissue layer/boundary, i.e. the regions of diseased tissue, from the determination of the fitted reference surface, or fitting on more than one region of the tissue layer/boundary or smoothing/filtering a tissue layer/boundary.

Still another aspect of the invention is to locate the general tissue layer/boundary contour for subsequent scans, which need to follow the tissue contour closely.

Additional aspects of the invention will be set forth in part in the description which follows. It is to be understood that both the foregoing general description and the following detailed description are exemplary and explanatory only and are not restrictive of the invention, as claimed.

DETAILED DESCRIPTION

Figure 3:
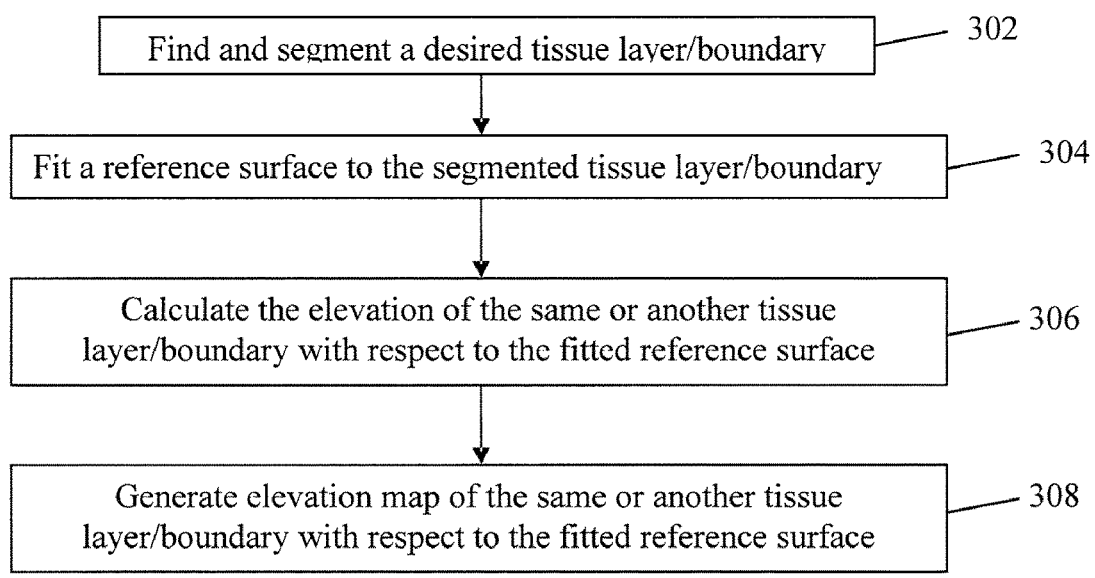
FIG. 3 shows a flow diagram of the steps of the invented image processing method.

FIG. 3 shows one preferred embodiment the presently invented method. This method is intended to be used on image data obtained from a sample. The illustrations in this application are based on image data derived from an optical coherence tomography system (OCT) which includes both time domain and spectral domain OCT systems. Such an instrument generates 3D intensity data corresponding to an axial reflection distribution arising from reflecting features in the eye. As noted above, this information is currently used by doctors to view and diagnosis various pathologies in the eye. A basic OCT system will be discussed below.

Although the illustrated embodiments are limited to OCT data, the image processing concepts described herein may be used with 3D image data derived from other modalities. For example, image data may be created using various forms of confocal microscopy and even ultrasound imaging modalities.

The first step in the subject method requires identification of a subset of the image data which corresponds to a boundary surface within the sample (step 302). As used herein, boundary surface can be a limiting surface in the sample, a surface of a layer or other interface. The boundary should have a sufficient linear or 2D extent that it can be reasonably fitted to a geometric line or surface.

Identification of the image data corresponding to a boundary surface is performed using a segmenting function. Methods for finding and segmenting a desired tissue layer or boundary surface are well-known in the art. (see for example, H. Ishikawa, et al., (2005) "Macular Segmentation with Optical Coherence Tomography". *Invest Ophthalmol Vis Sci.;* 46: 2012-201).

Once the image data corresponding to the selected surface has been segmented, the boundary is fitted to a substantially smooth reference surface (step 304). There are a number of well-known methods for fitting a measured surface data points to a geometric surface. One example is a second-order polynomial fit. Other functions, including Zernike or Chebyshev polynomials, Bessel functions, or a portion of a sphere or spheroid, can also be used for surface fitting. A smooth reference surface can be formed by fitting the shape of a tissue layer/boundary with a function of two variables. This requires a reasonably accurate segmentation of the chosen tissue layer/boundary and can be accomplished using, for example, a low-order polynomial fit in x and y.

The fitting may encompass the entire tissue layer/boundary or may be performed on various regions of the surface, e.g., fitting the foveal pit separately from the macula, or excluding pathological regions from the fitting. The reference surfaces can be used to define layers in the data that have the retinal tilt and curvature removed. In one aspect of the invention, these data points can be used to form en-face images representing retinal structures in those layers. This presents an advantage over the flat C-scan presentation of the data when imaging the curved layers in the anatomy of the eye, since a C-scan will only show tangential slices of the retinal layers.

As noted above, use of such a fitted surface can minimize the perturbations of the surface associated with disease so as to approximate the tissue surface that would exist if the tissue were normal. In this case, the fitting algorithm will function to reject points that are associated with the selected boundary surface but exist as a result of the disease. By using such a fitted surface, either of the tissue boundary being measured, or a different boundary, the effect of disease or injury is isolated from the overall shape of the tissue of interest, providing improved diagnostic information.

In the next step of the method (306), the distances or elevations between points on the reference surface and some other feature of interest are calculated. The feature of interest may be the actual boundary initially selected so that elevations will correspond to the deviations between the selected surface and the associated reference surface. The feature of interest can also be another interface or boundary within the sample.

Figure 5:
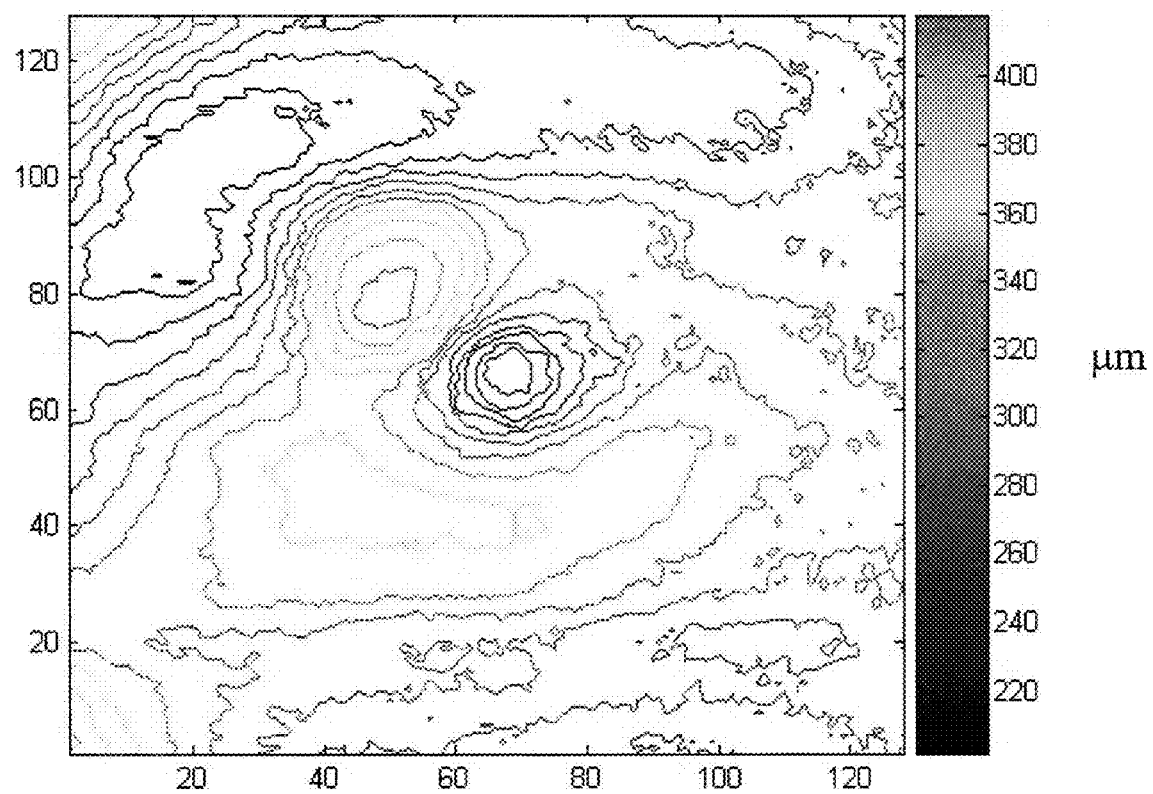
FIG. 5 shows a contour plot using the color coding that represents the distance from the ILM to a paraboloid fitted RPE reference surface.
Figure 6:
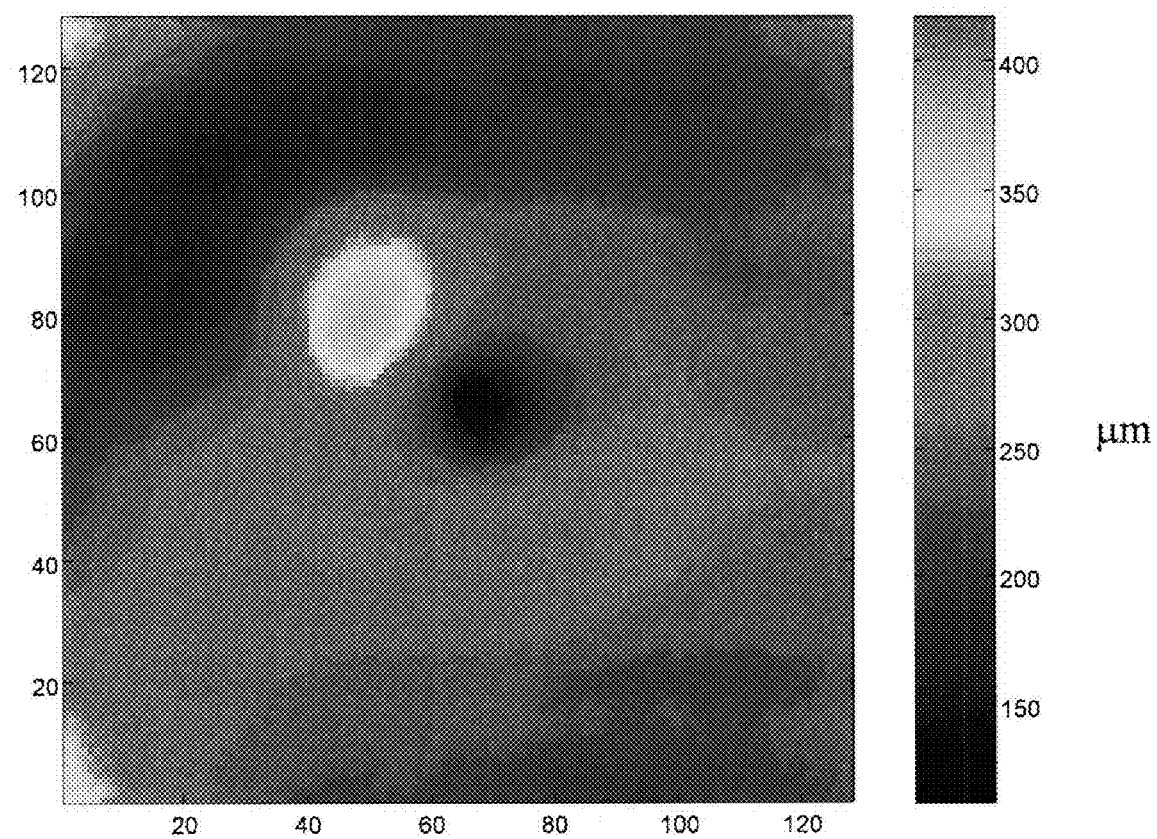
FIG. 6 shows a pseudocolor image representing the distance from the ILM to a paraboloid fitted RPE reference surface.

In the next step of the subject invention (308), 2D data sets are generated based on the calculated distances between the reference surface and other feature of interest. The 2D data sets can be used to create elevation maps. The elevation maps may be created based on pseudocolor or gray scales with elevation encoded as color as shown in FIG. 6 or intensity (not shown); or as topographical contour maps with elevation encoded as contour height as shown in FIG. 5 or as three dimensionally rendered topographical maps. These types of maps may also be combined to simultaneously display on the same map two sets of data, one for elevation relative to a fitted reference surface and the other for either another elevation relative to another reference surface, or an actual tissue layer thickness, or the originally collected image signal strength such as OCT or confocal optical signal strength for a tissue layer or other processed/unprocessed tissue layer/boundary data such as birefringence measured from a polarization sensitive OCT system or a scanning laser polarimetry system. For example, the distance from ILM relative to the RPE (i.e. the actual retina thickness) could be displayed as a contour map superimposed on a pseudocolor map of ILM elevation relative to a fitted RPE reference surface (not shown). Similarly, a pseudocolor map may be applied to a three-dimensional surface rendering in order to simultaneously display multiple information on elevation, thickness, reflectance or others.

In addition to the fact that by analyzing the curvature of the fitted reference surface, abnormal tissue layer curvatures (for example, the retina curvature for the case of pathologic myopia) can be diagnosed, the present invention has a number of other advantages over prior art methods as it can provide additional useful information for diagnosing diseased tissues. For example, the fitted reference surface can be used as a basis for elevation maps of retinal layers, to diagnose abnormal curvature of the retina, or as a guide for subsequent contour-following scans of that eye. Using such a fitted reference surface as a basis for "thickness" measurements could give more robust results because the exact topography of a deteriorating RPE may be more difficult to determine than the general shape of that layer. The reference surface determined by fitting will be more consistent than that determined by following the RPE in detail, especially in diseased eyes that may have breaks or complex variations in the RPE. As an example, map(s) of elevation can be displayed in the form of topographical contour map(s) applied to surface renderings of elevation. FIG. 5 shows a color contour coding that represents the distance from the ILM to a paraboloid reference surface fitted to the RPE. The corrected effective retinal "thickness" relative to the fitted surface is shown in microns on the color bar to the right of the map.

Figure 10:
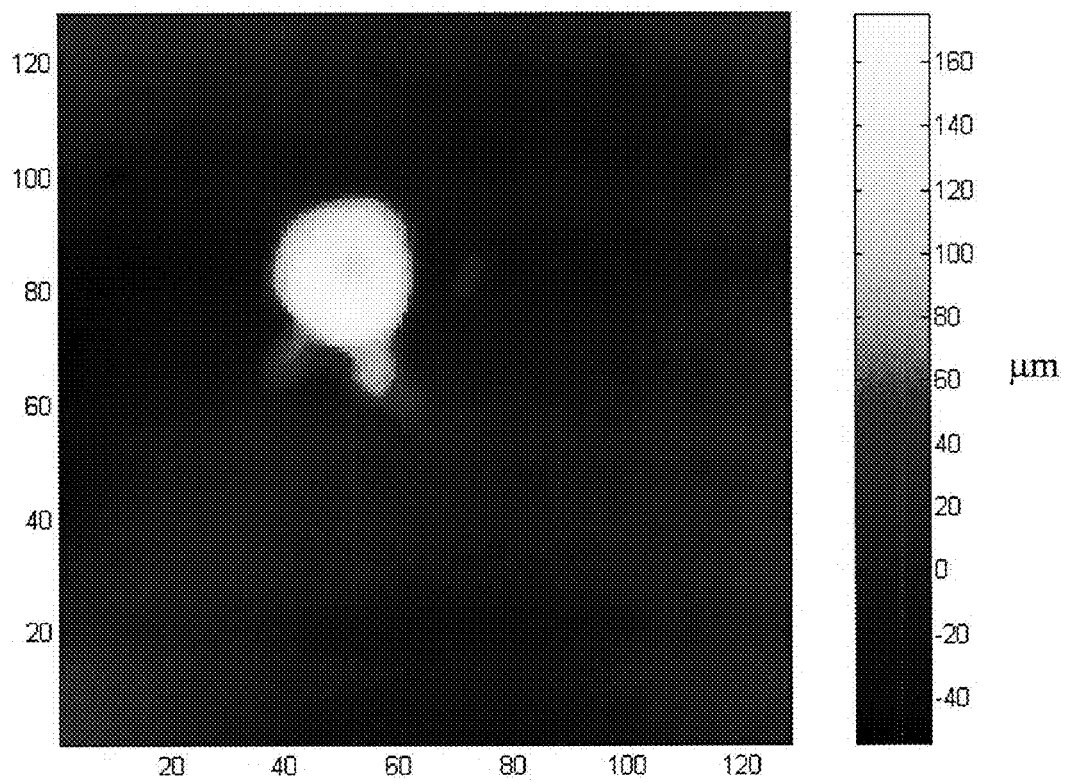
FIG. 10 shows a pseudocolor image representing the distance from the RPE to a paraboloid fitted RPE reference surface.

Additionally, presentation of topographic information relative to a fitted reference surface or surfaces can generate images with added information, for example:

(1) a 2-D false color image giving an en-face presentation of distance from the ILM to a reference surface fitted to the RPE can provide information on the effective retinal thickness which does not include thickness variations caused by small perturbations in the RPE. FIG. 6 shows a pseudocolor image representing the distance from the ILM to a paraboloid fitted RPE reference surface;

(2) a 2-D false color image giving an en-face presentation of distance from the actual RPE to a reference surface fitted to the RPE itself can highlight localized variations in the RPE which may be associated with disease. FIG. 10 shows a pseudocolor image representing the distance from the RPE to a paraboloid fitted RPE reference surface.

Figure 4:
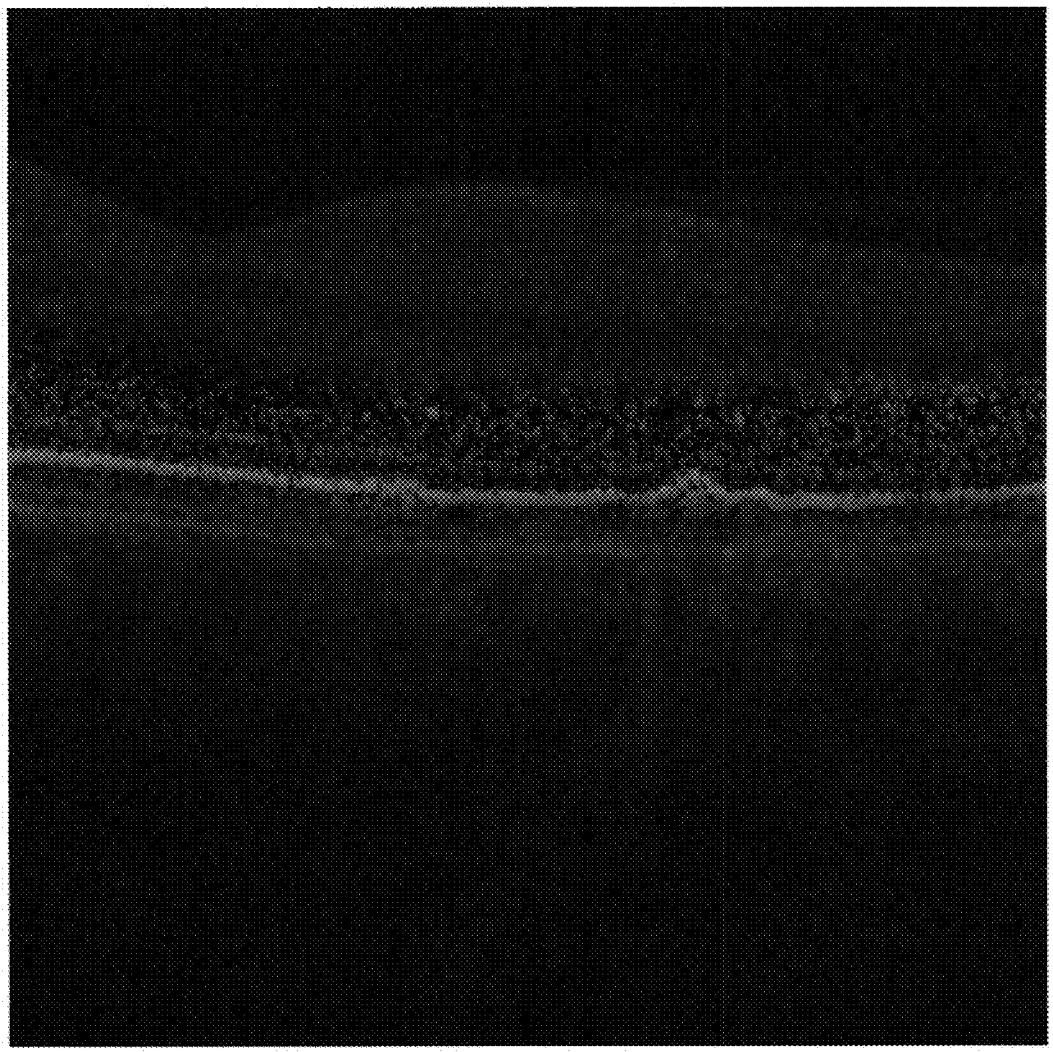
FIG. 4 shows a retina image with the hue mapped as the square of the distance from the fitted RPE reference surface.

(3) a color mapping for 2-D images or translucent 3-D renderings, in which brightness represents reflectance and hue represents distance from the reference surface, can provide an illustration of the height of brightly reflecting layers from the reference surface without detailed segmentation of all the layers. For cases of complicated pathology, fully automated segmentation algorithms for multiple layers may be too time-consuming for routine use and manual user intervention may not be practical. For example, in the case of an RPE detachment, the layers that are normally brightly reflecting very near to the reference surface are now very far removed from the reference surface. The human eye is very sensitive to hue changes, and a convenient way to illustrate such RPE detachment is to use hue changes. FIG. 4 shows a 2-D retina image with the hue mapped as the square of the distance from the fitted RPE reference surface.

Figure 7:
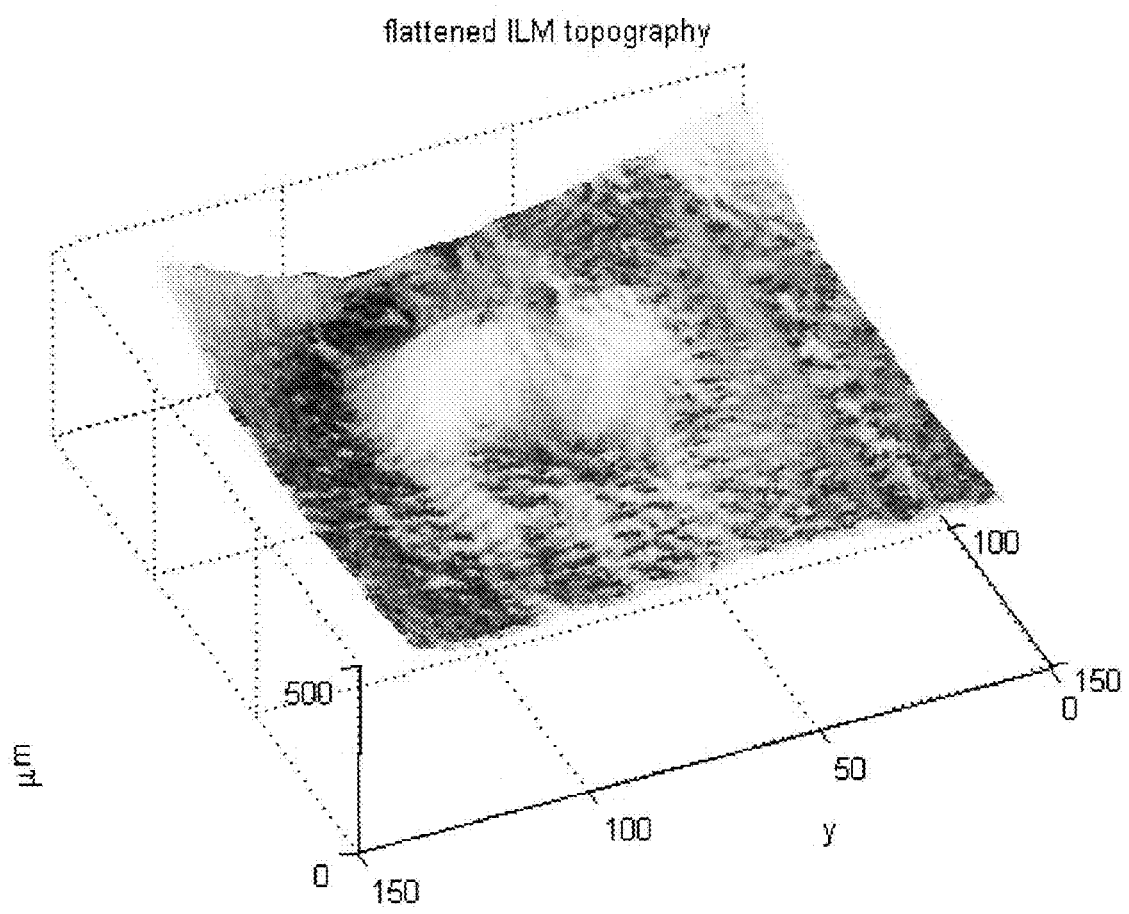
FIG. 7 shows a three-dimensional rendering of the ILM surface elevation relative to the paraboloid fitted RPE reference surface, with the color indicating in duplicate the same elevation information.

(4) a flattened 3-D rendering of a retinal surface or surfaces, which shows the elevation relative to a reference surface rather than its actual contour elevation in the image data can provide a more meaningful view of the retina anatomic features. FIG. 7 shows a three-dimensional rendering of the ILM elevation relative to a paraboloid fitted RPE reference surface. Different pupil positions cause tilt in the recorded retinal images, and variations in working distance cause different curvature in the recorded retinal images. Warping the OCT data to flatten this image may have advantages for more standardized presentation, regardless of exact pupil and z position, aiding comparisons of the images between visits, or registration of multiple scans for other purposes such as speckle reduction.

Figure 8:
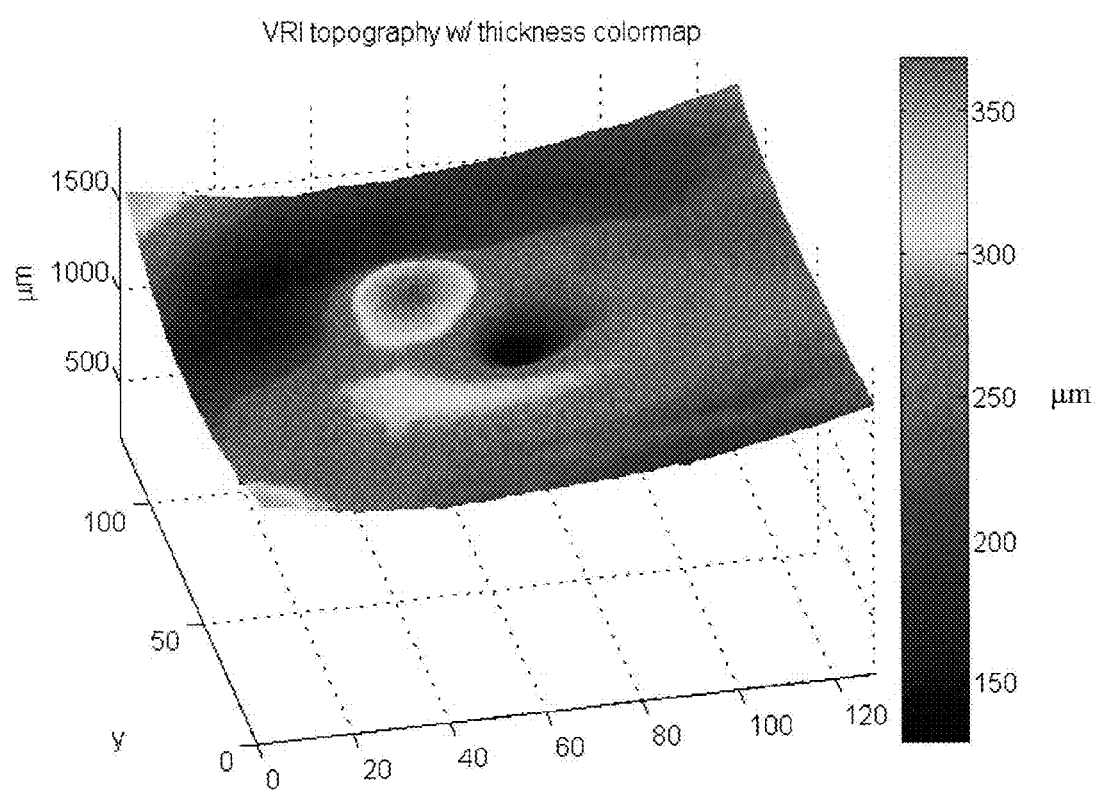
FIG. 8 shows a three-dimensional rendering of the actual retina thickness superimposed with a pseudocolor image indicating ILM elevation with respect to the paraboloid fitted RPE reference surface
Figure 9:
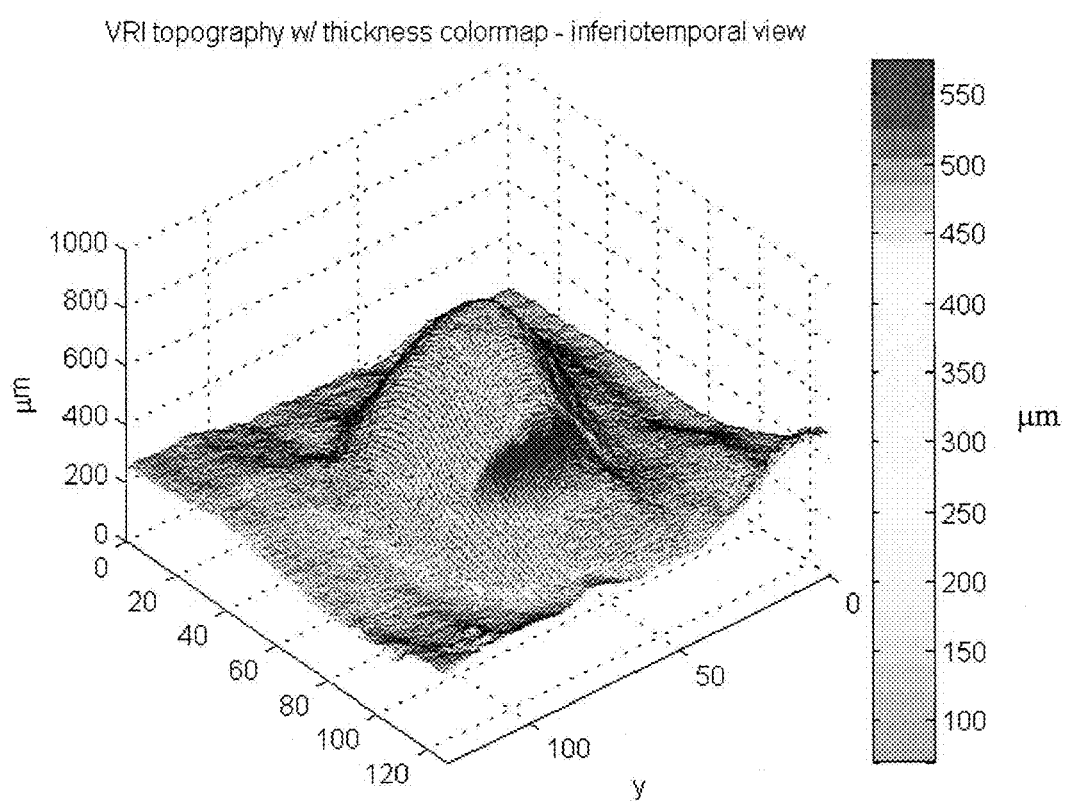
FIG. 9 shows a three-dimensional rendering of the ILM surface elevation relative to the paraboloid fitted RPE reference surface superimposed with a pseudocolor image indicating actual retinal thickness.

(5) a 3-D rendering of the ILM with a color mapping for elevation relative to the reference surface fitted to the RPE can combine the false color image previously described in (1), along with the actual retina thickness which could indicate the presence of traction by membranes on its surface. FIG. 8 shows a three-dimensional rendering of the actual retina thickness superimposed with a pseudocolor image indicating ILM elevation with respect to the paraboloid fitted RPE reference surface. On the other hand, such a superimposed 3D rendering can also be the other way round. For example, FIG. 9 shows a three-dimensional rendering of the ILM surface elevation relative to the paraboloid fitted RPE reference surface superimposed with a pseudocolor image indicating actual retinal thickness. The ILM elevation may reflect the position in the image data or a rendering that is flattened to a reference surface as previously described in (4).

Axial resolution may be wasted if the z-range of the scan does not follow the contour of the retinal tissue. A few initial scans could be used to determine the reference surface, then a retina-following scan could be performed by changing the OCT reference arm length to follow the predetermined reference surface as the transverse scans are performed.

Note that the present invention can also be applied to B-scan images in which case, the term reference surface should interpreted as a reference curved line and tissue layer/boundary will also be interpreted as a curved line. FIG. 4 shows a B-scan retina image with the hue mapped as the square of the distance from the fitted RPE reference surface. The vertical distance in the image relative to the location of the fitted RPE reference surface is encoded as a color which is used to highlight the image.

The present invention does not need to follow the exact sequence as shown in FIG. 3, as other additional steps can be inserted to perform substantially equivalent operations. For example, the fitting operation may be approximated by smoothing or otherwise filtering the retinal layer. Also, the reference surface might not be the direct result of fitting, but some filtered version thereof. Furthermore, a variation of this idea could use two such reference surfaces, rather than the elevation from an unfitted surface to a reference surface.

The presently invented method could be applied to the analysis of the retina or curvature of the eye in existing and future OCT systems. It can also be used for analysis of other biological tissues such as the skin. Also, it may find use in ultrasound and confocal microscopy systems as well.

Figure 11:
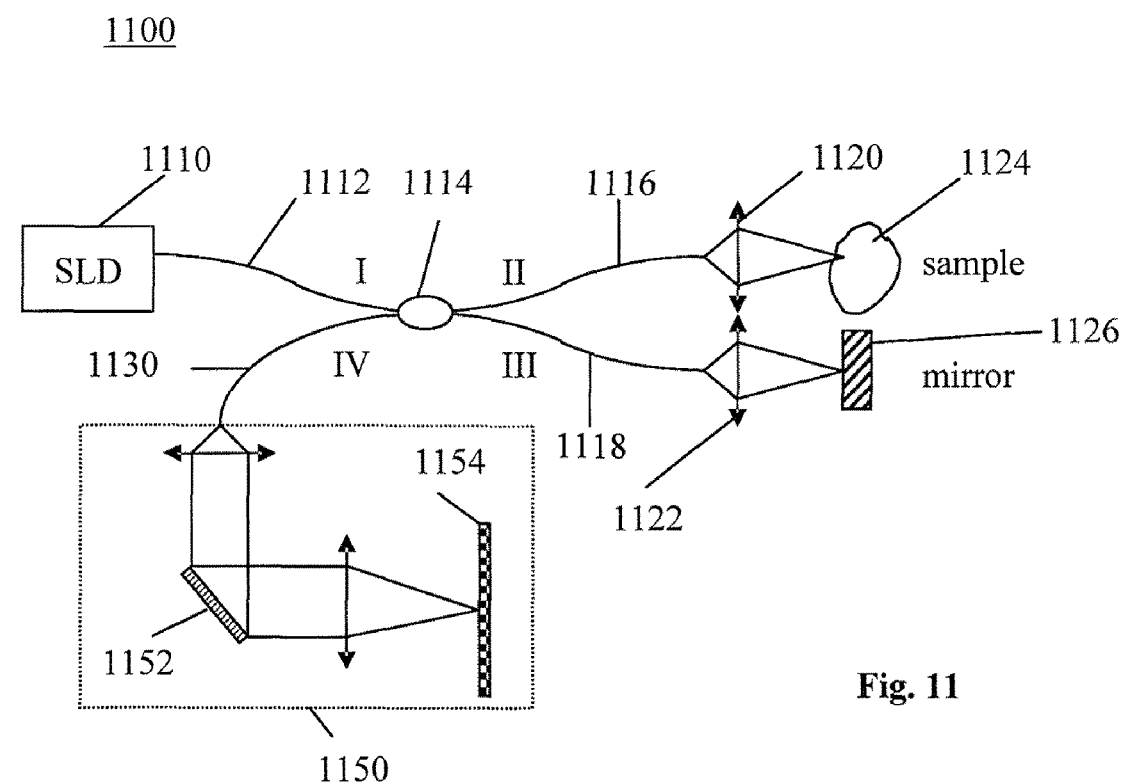
FIG. 11 is a schematic diagram of a basic OCT system capable of generating 3D image data that can be used in the method of the subject invention.

FIG. 11 shows a basic spectrometer based spectral domain OCT system 1100. The light wave from the broadband emitter 1110 is preferably coupled through a short length of an optical fiber 1112 to an input port (port I) of a fiber optic coupler 1114, which splits the incoming light beam into the two arms of a Michelson interferometer. The two arms each have a section of optical fiber (1116 and 1118) that guides the split light beam from the two output ports (port II and port III) of the fiber coupler 1114 to a sample 1124 and a reference reflector 1126 respectively. For both the sample arm and the reference arm, at the terminating portion of each fiber, there may be a module containing optical elements to collimate or focus or scan the beam. Illustrated in FIG. 11 as an embodiment are two focusing lenses 1120 and 1122. The returned light waves from the sample 1124 and the reference reflector 1126 are directed back through the same optical path of the sample and reference arms and are combined in fiber coupler 1114. A portion of the combined light beam is directed through a section of optical fiber 1130 from port IV of the fiber coupler 1114 to a spectrometer 1150. Inside the spectrometer, the light beam is dispersed by a grating 1152 and focused onto a detector array 1154. Note that the principle of operation of a tunable laser based swept source OCT is very similar to that of a spectrometer based spectral domain OCT system (see for example, Choma, M. A. et al. (2003). "Sensitivity advantage of swept source and Fourier domain optical coherence tomography." *Optics Express* 11(18): 2183-2189), hence the spectral domain OCT system for obtaining the 3D image data set can also be a swept source OCT system.

Although various embodiments that incorporate the teachings of the present invention have been shown and described in detail herein, those skilled in the art can readily devise many other varied embodiments that still incorporate these teachings.

The following references are hereby incorporated by reference:

US PATENT DOCUMENTS

U.S. Pat. No. 4,838,679
U.S. Pat. No. 5,293,871
U.S. Pat. No. 5,562,095
U.S. provisional patent application, Ser. No. 60/632,387

OTHER PUBLICATIONS

Adaikkappan, M. et al., (2002) "Evaluation of Carotid Atherosclerosis by B-Mode Ultrasonographic Study in Hypertensive Patients Compared with Normotensive Patients" *Ind J Radiol Imag;* 12:3:365-368.
Bartsch, D. G. et al., (2004) "Optical coherence tomography: interpretation artifacts and new algorithm", *Proc. SPIE Medical Imaging* 2004: *Image Processing,* 5370: 2140-2151.
Choma, M. A. et al. (2003). "Sensitivity advantage of swept source and Fourier domain optical coherence tomography." *Optics Express* 11(18): 2183-2189
Ishikawa, H. et al., (2005) "Macular Segmentation with Optical Coherence Tomography". *Invest Ophthalmol Vis Sci.;* 46: 2012-201.
Webb, R. H. (1996) "Confocal optical microscopy" *Rep. Prog. Phys.* 59 427-471.
Zhou, Q. et al. (2004). "Mapping retinal thickness and macular edema by high-speed three-dimensional optical coherence tomography". Ophthalmic Technologies XIV, SPIE, 5314: 119-125.

We claim:

1. A method for generating image maps from a 3D image data set, said data set obtained from imaging an eye using an imaging device, said eye having at least one boundary surface associated therewith, said method comprising the steps of:
   identifying a boundary surface within the 3D image data set;
   generating a substantially smooth reference surface from the boundary surface;
   identifying a second surface within the 3D image data set;
   calculating the distance between points on the smooth reference surface and corresponding points on the second surface;
   generating an image map of the calculated distances; and
   displaying the image map.

2. A method as recited in claim 1, wherein the boundary surface is the RPE.

3. A method as recited in claim 1, wherein the boundary surface is the front surface of the cornea.

4. A method as recited in claim 1, wherein the boundary surface is the ILM.

5. A method as recited in claim 1, wherein the substantially smooth reference surface is generated by fitting the boundary surface.

6. A method as recited in claim 1, wherein the substantially smooth reference surface is generated by smoothing the boundary surface.

7. A method as recited in claim 1, wherein the substantially smooth reference surface is generated by filtering the boundary surface.

8. A method for generating en-face images representing retinal structures in the eye from a 3D image data set, said data set obtained from imaging an eye using an imaging device, said eye having at least one boundary surface associated therewith, said method comprising the steps of:
   identifying a boundary surface within the 3D image data set;
   generating a substantially smooth reference surface from the boundary surface;
   defining a layer in the 3D data set using the smooth reference surface in order to remove retinal tilt and curvature from said layer;
   generating an en-face image using data points within the defined layer; and
   displaying the en-face image.

9. A method as recited in claim 8, wherein the boundary surface is the RPE.

10. A method as recited in claim 8, wherein the boundary surface is the front surface of the cornea.

11. A method as recited in claim 8, wherein the boundary surface is the ILM.

12. A method as recited in claim 8, wherein the substantially smooth reference surface is generated by fitting the boundary surface.

13. A method as recited in claim 8, wherein the substantially smooth reference surface is generated by smoothing the boundary surface.

14. A method as recited in claim 8, wherein the substantially smooth reference surface is generated by filtering the boundary surface.

15. A method as recited in claim 8, wherein the substantially smooth reference surface is generated using at least one selected region of the boundary surface.

16. A method as recited in claim 8, wherein the substantially smooth reference surface is generated by excluding at least one region of the boundary surface.

17. A method as recited in claim 8, wherein the layer in the 3D data set is defined using a second surface in addition to the smooth reference surface.

18. A method for generating image maps from a 3D image data set, said data set obtained from imaging an eye using an imaging device, said eye having at least one boundary surface associated therewith, said method comprising the steps of:
   identifying a boundary surface within the 3D image data set;
   selecting at least one region of the boundary surface;
   generating a substantially smooth reference surface to the 3D image data using the at least one selected region of the boundary surface;
   identifying a second surface within the 3D image data set;
   calculating the distance between points on the smooth reference surface and corresponding points on the second surface;
   generating an image map of the calculated distances; and
   displaying the image map.

19. A method as recited in claim 18, wherein the substantially smooth reference surface is generated by fitting the boundary surface.

20. A method as recited in claim 18, wherein the substantially smooth reference surface is generated by smoothing the boundary surface.

21. A method as recited in claim 18, wherein the substantially smooth reference surface is generated by filtering the boundary surface.

22. A method as recited in claim 18, further comprising displaying the difference between the smooth reference surface and the boundary surface.

23. A method for generating image maps from a 3D image data set, said data set obtained from imaging an eye using an imaging device, said eye having at least one boundary surface associated therewith, said method comprising the steps of:
   identifying a boundary surface within the 3D image data set;
   excluding at least one region of the boundary surface;
   generating a substantially smooth reference surface to the 3D image data over the remaining regions of the boundary surface;
   identifying a second surface within the 3D image data set;
   calculating the distance between points on the smooth reference surface and corresponding points on the second surface;
   generating an image map of the calculated distances; and
   displaying the image map.

24. A method as recited in claim 23, wherein the substantially smooth reference surface is generated by fitting the boundary surface.

25. A method as recited in claim 23, wherein the substantially smooth reference surface is generated by smoothing the boundary surface.

26. A method as recited in claim 23, wherein the substantially smooth reference surface is generated by filtering the boundary surface.

27. A method as recited in claim 23, wherein the at least one region of the boundary surface is excluded based on a perturbation of the tissue of the eye in that region.

28. A method as recited in claim 27, wherein the perturbation is an abnormality of the tissue.

29. A method as recited in claim 27, wherein the perturbation is a local variation of the tissue.

30. A method as recited in claim 27, wherein the perturbation is an abrupt change in the tissue direction.

31. A method for generating image maps from a 3D image data set, said data set obtained from imaging an eye using an imaging device, said eye having at least one boundary surface associated therewith, said method comprising the steps of:
   identifying a boundary surface located within the retina in the 3D image data set;
   generating a substantially smooth reference surface from the boundary surface;
   identifying a second surface within the retina in the 3D image data set;
   calculating the distance between points on the smooth reference surface and corresponding points on the second surface;
   generating an image map of the calculated distances; and
   displaying the image map.

32. A method as recited in claim 31, wherein the substantially smooth reference surface is generated by fitting the boundary surface.

33. A method as recited in claim 31, wherein the substantially smooth reference surface is generated by smoothing the boundary surface.

34. A method as recited in claim 31, wherein the substantially smooth reference surface is generated by filtering the boundary surface.

* * * * *

UNITED STATES PATENT AND TRADEMARK OFFICE
CERTIFICATE OF CORRECTION

| | | |
|---|---|---|
| PATENT NO. | : 8,073,202 B2 | Page 1 of 1 |
| APPLICATION NO. | : 12/709234 | |
| DATED | : December 6, 2011 | |
| INVENTOR(S) | : Matthew J. Everett et al. | |

It is certified that error appears in the above-identified patent and that said Letters Patent is hereby corrected as shown below:

On page 2, under "OTHER PUBLICATIONS", in column 1, line 5, delete "tomographny" and insert -- tomography --, therefor.

Figure 1:
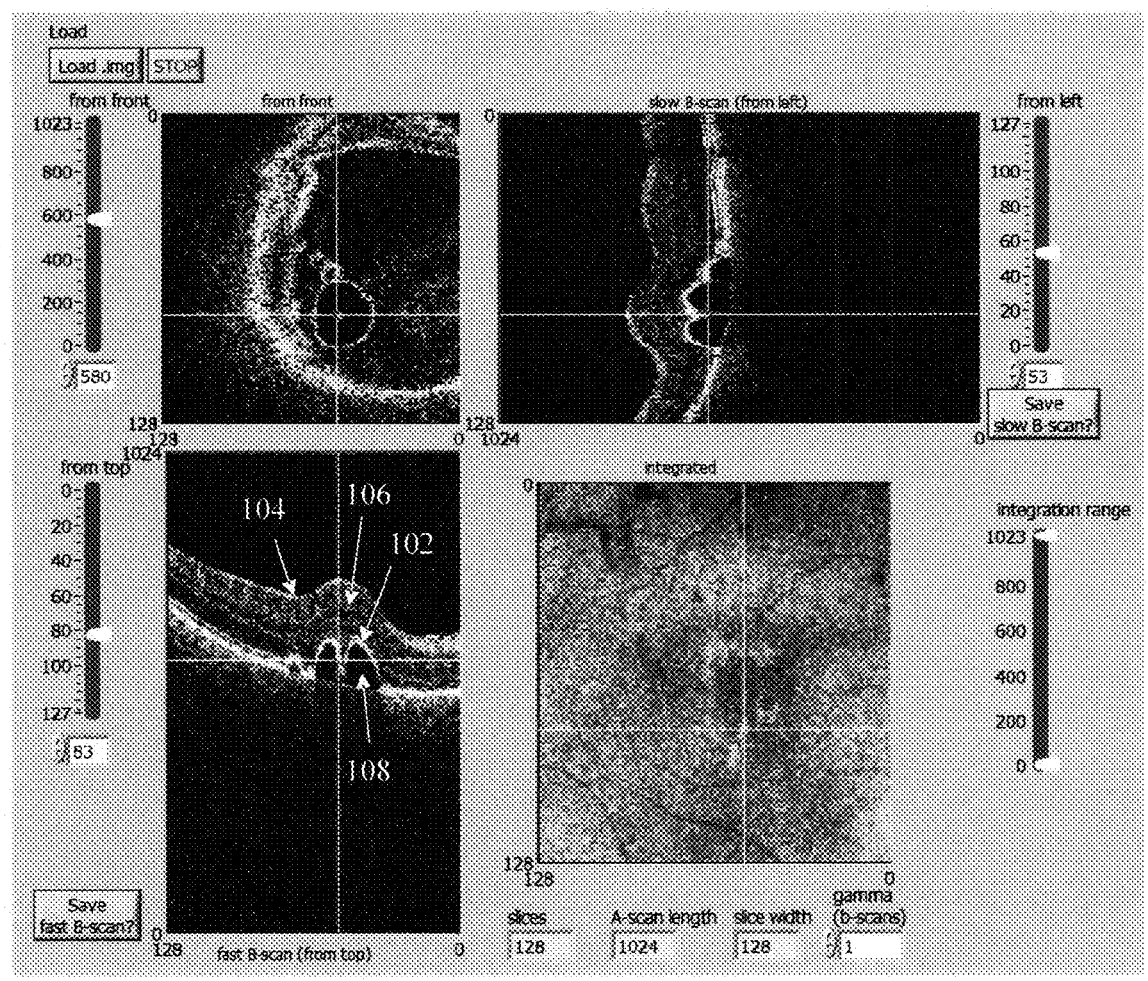
FIG. 1 shows OCT images of a retina, illustrating RPE (retinal pigment epithelium), the ILM (inner limiting membrane), a sharp bump and a lesion below the sharp bump.
Figure 2:
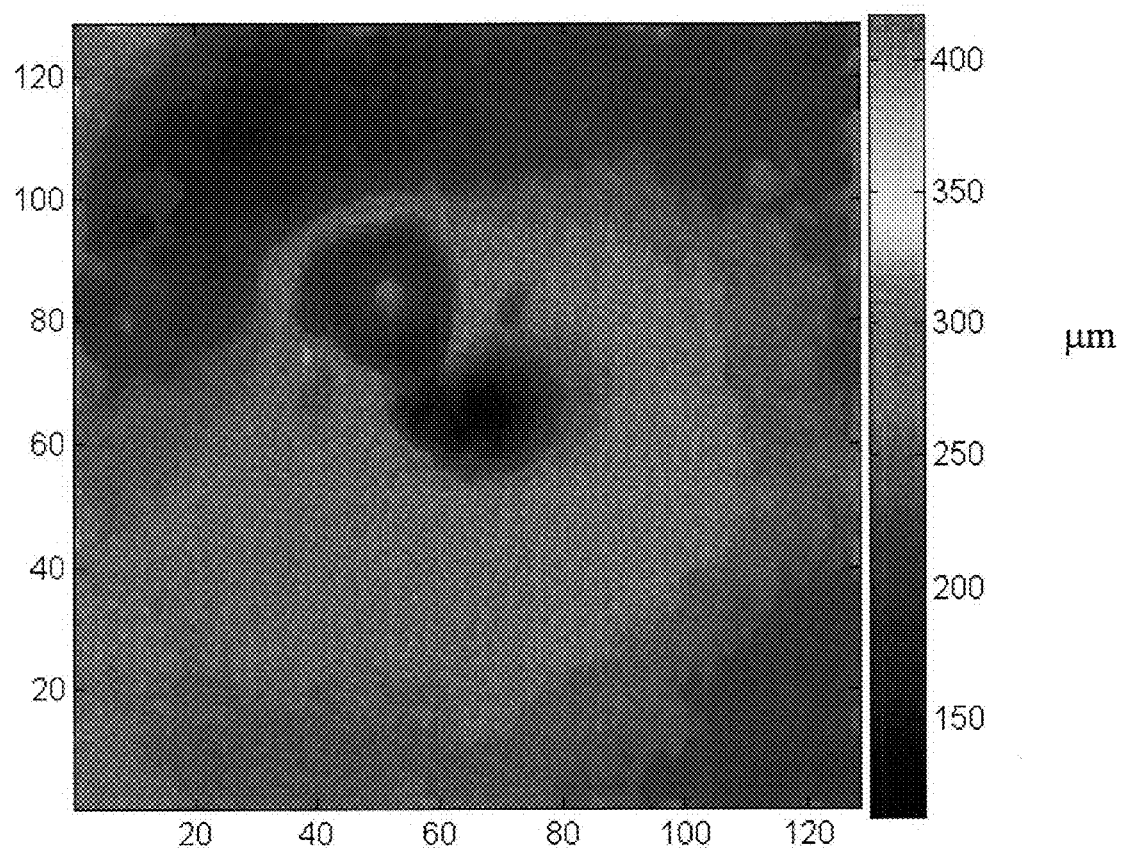
FIG. 2 is a color coded retina thickness map corresponding to FIG. 1

In column 3, line 30, delete "FIG. 1" and insert -- FIG. 1. --, therefor.

In column 3, line 34, delete "surface;" and insert -- surface. --, therefor.

In column 3, line 37, delete "surface;" and insert -- surface. --, therefor.

In column 3, line 40, delete "surface;" and insert -- surface. --, therefor.

In column 3, line 48, delete "surface" and insert -- surface. --, therefor.

In column 3, line 52, delete "thickness;" and insert -- thickness. --, therefor.

In column 5, line 60, delete "surface;" and insert -- surface. --, therefor.

In column 8, line 3, delete "2183-2189" and insert -- 2183-2189. --, therefor.

Signed and Sealed this

Thirteenth Day of March, 2012

David J. Kappos
*Director of the United States Patent and Trademark Office*